United States Patent [19]
Fujita et al.

[11] Patent Number: 4,798,844
[45] Date of Patent: Jan. 17, 1989

[54] CHEMOTHERAPEUTANT COMPOSITION

[75] Inventors: Takayuki Fujita, Matsushige; Yoshiya Iwasaki, Kitajima; Hiroko Yabe, Tokushima, all of Japan

[73] Assignee: Shikoku Chemicals Corporation, Kagawa, Japan

[21] Appl. No.: 38,006

[22] Filed: Apr. 14, 1987

[30] Foreign Application Priority Data

Feb. 20, 1987 [JP] Japan ................................. 62-38750
Apr. 4, 1987 [JP] Japan ................................. 62-82224

[51] Int. Cl.$^4$ ........................................... A61K 31/415
[52] U.S. Cl. .................................................. 514/399
[58] Field of Search ......................................... 514/399

[56] References Cited
PUBLICATIONS

Chemical Abstracts 87:68368c (1977).

Primary Examiner—Jerome D. Goldberg
Attorney, Agent, or Firm—Sherman and Shalloway

[57] ABSTRACT 1-(4-Chlorophenyl)-2-(1H-imidazolyl)-3-(2,4-dichlorophenyl)-2-propen-1-one hydrochloride is useful as a chemotherapeutant which is administered to men or animals for remedy of diseases caused by true fungi or bacteria.

10 Claims, No Drawings

CHEMOTHERAPEUTANT COMPOSITION

BACKGROUND OF THE INVENTION (1) Field of the Invention

The present invention relates to a chemotherapeutant composition to men or animals. More particularly, the present invention relates to a chemotherapeutant composition which is useful for remedy of infectious diseases by true fungi or bacteria and especially suitable for oral administration.

(2) Description of the Prior Art

In Chemical Abstracts, 87, 68368c (1977) (German Patent Laid-Open Specification No. 2,645,617), it is taught that an imidazole compound represented by the following formula:

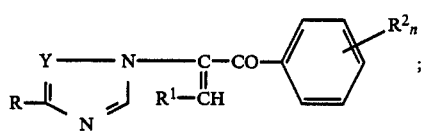

wherein R stands for a hydrogen atom or a nitro group, $R^1$ stands for a propyl, phenyl, substituted phenyl, 2-furyl or 2-thienyl group, $R^2{}_n$ stands for a hydrogen atom, or 4-Cl, 4-F, 4-phenyl or 2,4-Cl$_2$, and Y stands for a nitrogen atom or a CH group,
is valuable as a fungicide, and that if barley is treated with a spray containing this imidazole compound, infection with Erysiph graminis can be completely controlled.

SUMMARY OF THE INVENTION

We found that among the above-mentioned compounds, 1-(4-chlorophenyl)-2-(1H-imidazolyl)-3-(2,4-dichlorophenyl)-2-propen-1-one hydrochloride is valuable as a chemotherapeutant to infectious diseases by true fungi or bacteria in men or animals, which are different from plants in the kinds of infectious bacteria. It also was found that the above-mentioned specific compound is useful as a chemotherapeutant which is orally administered to men or animals. We have now completed the present invention based on these findings.

In accordance with one aspect of the present invention, there is provided a chemotherapeutant composition for men or animals, which comprises 1-(4-chlorphenyl)-2-(1H-imidazolyl)-3-(2,4-dichlorophenyl)-2-propen-1-one hydrochloride as the effective ingredient and a pharmaceutical additive.

In accordance with another aspect of the present invention, there is provided a chemotherapeutant composition which is orally administered to men or animal in the form of a capsule, a granule, a pill, a powder, a tablet or a troche, said composition comprising 1-(4-chlorophenyl)-2-(1H-imidazolyl)-3-(2,4-dichlorophenyl)-2-propen-1-one hydrochloride as the effective ingredient and a pharmaceutical additive.

DETAILED DESCRIPTION OF THE PREFERRED EMBODIMENT

The above-mentioned compound used as the effective ingredient in the present invention is represented by the following formula:

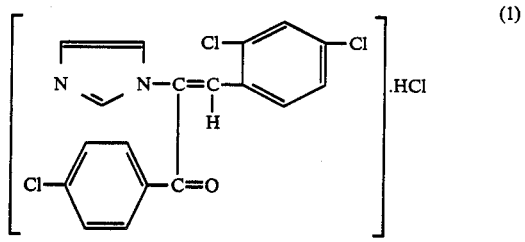

The compound of the formula (1) is obtained by reacting 2(1H-imidazolyl)-4'-chloroacetophenone with 2,4-dichlorobenzaldehyde.

This compound is a white crystal having the following physical properties.

Melting Point: 177° to 179° C.

TLC (chloroform/methanol=10/1): Rf=0.55.

Infrared Absorption Spectrum Analysis (cm$^{-1}$): 1650 (C=O).

Nuclear Magnetic Resonance Analysis (dimethylsulfoxide, —d$_6$, ppm):
6.93–7.08 (2H, d, 4,5-positions of imidazole),
7.25–7.39 (2H, dd, 2-position of imidazole, =CH),
7.55–7.81 (5H, m, aromatic), 7.94–8.09 (2H, d,

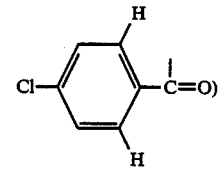

This effective ingredient is used in the form of an orally administrable preparation such as a capsule, a granule, a pill, a powder, a tablet or a troche in combination with a pharmaceutical additive. As the carrier, there can be used at least one member selected from excipients such as Kaolin, licorice powder, natural aluminum silicate, magnesium silicate, light anhydrous silicic acid, dry aluminum oxide gel, heavy magnesium oxide, precipitated calcium carbonate, magnesium carbonate, sodium hydrogencarbonate, calcium lactate, sodium hydrogenphosphate, calcium hydrogenphosphate, gypsum, calcined gypsum, talc, crystalline cellulose, dextrin, lactose, glucose, D-sorbitol, starch, agar and bentonite, binders such as gum arabic, carboxymethyl cellulose, hydroxypropyl cellulose, methyl cellulose, tragacanth gum and stearic acid, disintegrating agents such as sodium alginate and enzymes, lubricants such as carnauba was, hardened oil, sesame oil, bleached bees wax, titanium oxide, calcium stearate, magnesium stearate and polyethylene glycol, and coating agents such as olive oil, hardened oil, paraffin, carnauba wax, gelatin, refined shellac and white shellac. Furthermore, colorants, taste-improving agents, smell-improving agents, antioxidants and stabilizers may be incorporated according to need. In the case where the active ingredient is used in the form of a capsule, there can be used capsules composed mainly of water-soluble polymers such as gelatin.

In case of a solid preparation, in order to adjust the absorption of the effective ingredient, a stomach-soluble coating, an entrail-soluble coating (enteric coating) or an absorbing base may be formed.

In case of a solid preparation, the concentration of the effective ingredient is not particularly critical, but the concentration of the effective ingredient can be 1 to 80% by weight, especially 10 to 40% by weight.

Furthermore, the effective ingredient of the present invention can be orally administered in the form of a liquid. In this case, refined water is mainly used as the additive. In case of an elixir, however, ethanol may be used in an amount of 8 to 10% or 73 to 78%. Furthermore, glycerol is used in addition to ethanol and acts also as a sweetening agent. In this case, a preservative agent, a suspending agent, a tackifier, a sweetening agent, a perfume and a colorant may be added singly or in combination, if desired. The concentration of the effective ingredient is 1 to 40% by weight, especially 5 to 20% by weight.

The chemotherapeutant composition of the present invention can also be used in the form of a medicine for external application, for example, a liquid such as a lotion or a semi-solid preparation such as a hard ointment, a suppository or a soft ointment. In this case, as the base, there can be used oily bases such as hydrous lanolin, vaseline, paraffin plaster and other waxes, water-soluble bases such as glycerol, glycolic acid, polyethylene glycol and gelatin, and oil-in-water type emulsion bases and water-in-water type emulsion bases. A stabilizer, an antiseptic agent, a preservative agent, an emulsifier and a suspending agent may be added according to need.

In case of a medicine for external application, it is preferred that the concentration of the effective ingredient be 0.1 to 10% by weight, especially 0.5 to 2% by weight.

Furthermore, the chemotherapeutant composition can be used in the form of an injection. In this case, as the base, there can be used aqueous solvents such as distilled water for injection, physiological saline solution and Ringer's solution, and non-aqueous solvents such as a plant oil. The base may be mixed with at least one member selected from stabilizers, for example, inert gases such as nitrogen gas, reducing substances such as sodium thiosulfate and chelating agents such as ethylenediamine-tetraacetic acid (EDTA), preservative agents such as p-hydroxybenzoic acid, solvent-soluble adjuvants such as ethanol, propylene glycol and polyethylene glycol, surface active agents such as Tween 80, isotonizing agents such as sodium chloride, analgesic agents such as procaine hydrochloride, buffer agents or pH-adjusting agents, suspending agents, and tackifiers. In case of an injection, the concentration of the effective ingredient is 0.025 to 0.5%by weight, especially 0.05 to 0.2% by weight.

The chemotherapeutant composition of the present invention has an excellent anti-microbial activity to pathogenic true fungi such as *Candida, Trichophyton* and *Microsporum* and pathogenic bacteria such as *Staphylococcus, Streptococcus* and *Bacillus subtilis*. The chemotherapeutant composition of the present invention can be applied to men or animals by oral administration, external administration, injection or a combination thereof.

When the chemotherapeutant of the present invention is orally administered, it migrates in blood, and therefore, the chemotherapeutant of the present invention is especially suitable for oral administration to men or animals.

The amount administred of the chemotherapeutant of the present invention is changed according to the disease condition or the administration form, but in general, the chemotherapeutant composition of the present invention is administred in an amount of 1 to 300 mg/kg of the body weight per day, especially 5 to 150 mg/kg of the body weight per day.

The present invention wlil now be described in detail with reference to the following examples.

EXAMPLE 1

Preparation of 1-(4-chlorophenyl)-2-(1H-imidazolyl)-3-(2,4-dichlorophenyl)-2-propen-1-one hydrochloride.

To a solution of 3.3 g of 2-(1H-imidazolyl)-4'-chloroacetophenone and 2.7 g of 2,4-dichlorobenzaldehyde in anhdyrous benzene was added 0.5 ml of piperidine, and a Dean-Stalk trap was attached to a reactor and the mixture was refluxed for 5 hours. The solvent was removed by distillation under reduced pressure, and the residue was washed with petroleum ether two times and a hydrochloric acid-ethanol solution was added to adjust the pH value to 1. The mixture was refluxed for 5 minutes and the solvent was removed by distillation under reduced pressure, and ether was added to the residue to precipitate a crystal. Recrystallization from isopropanol gave 3.8 g of a white crystal having a melting point of 177° to 179° C. From the results of analysis, it was confirmed that the product was 1-(4-chlorophenyl)-2-(1H-imidazolyl)-3-(2,4-dichlorophenyl)-2-propen-1-one hydrochloride having the following structural formula. The yield was 61%.

Structural Formula:

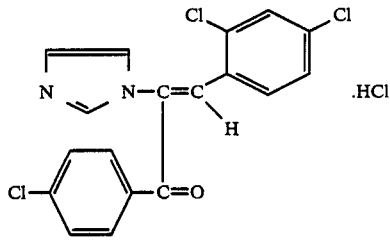

Results of Analysis:

Elementary analysis as $C_{18}H_{11}N_2OCl_3$ HCl). Found values: C=52.29%, H=2.79%, N=6.47%. Calculated values: C=52.21%, H=2.92%, N=6.76%.

TLC (chloroform/methanol=10/1) Rf: 0.55.

Infrared absorption spectrum analysis (cm$^{-1}$) 1650 (C=O).

Nuclear magnetic resonance analysis (dimethylsulfoxide, —d$_6$, ppm): 6.93–7.08 (2H, d, 4,5-positions of imidazole), 7.25–7.39 (2H, dd, 2-position of imidazole, =CH), 7.55–7.81 (5H, m, aromatic), 7.94–8.09 (2H, d,

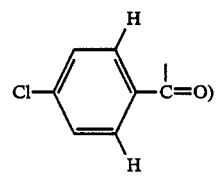

EXAMPLE 2

Antimicrobial Activity to Pathogenic True Fungi

A true fungus shown in Table 1 was cultured in Sabourauds agar medium at 25° C. for 7 to 14 days, and the minimum inhibitory concentration (MIC value, μg/ml) was determined. The obtained results are shown in Table 1.

TABLE 1

| Pathgenic True Fungus | MIC Value (μg/ml) |
|---|---|
| Candida albicans | <6.25 |
| Trichophyton rubrum | <1.25 |
| Trichophyton mentagrophytes | <1.25 |
| Trichophyton tonsurans | <1.25 |
| Microsporum gypseum | <1.25 |
| Aspergillus niger | 3.12 |
| Aspergillus fumigatus | 3.12 |

EXAMPLE 3

Antimicrobial Activity to Pathogenic Bacteria

The minimum inhibitory concentrations to pathogenic bacteria shown in Table 2 were determined by the agar plate dilution process according to the standard method of the Japanese Chemotherapeutic Association. The obtained results are shown in Table 2.

TABLE 2

| Pathogenic Bacterium | MIC Value (μg/ml) |
|---|---|
| Staphylococcus aureus | 1.56 |
| Streptococcus pyogenes | 3.12 |
| Streptococcus faecalis | 3.12 |
| Bacillus subtilis | 3.12 |

EXAMPLE 4

Migration in Blood

The compound obtained in Example 1 was orally administered at a dose of 300 mg/kg in the form of a suspension in gum arabic to a rat, and the change of the concentration in blood was examined by the high-speed liquid chromatography. The obtained results are shown in Table 3. It is seen that the compound has a property of migrating in blood and a maximum concentration in blood can be obtained within several hours after the administration.

TABLE 3

| Elapsing Time (hours) | Concentration (μg/ml) in Blood |
|---|---|
| 0 | 0 |
| 2 | 1.20 |
| 4 | 2.97 |
| 6 | 9.07 |
| 8 | 4.26 |
| 12 | 5.62 |
| 24 | 1.50 |

NOTE

Each value is the concentration of the compound bonded with a blood protein having a small molecular weight (fraction molecular weight=10,000).

EXAMPLE 5

Curative Effect to Candidiasis

A mouse was infected with Candida albicans, and when 1.4 hours had passed from the infection, the compound obtained in Example 1 was orally administered in the form of a suspension in gum arabic. After two days, the pharmaceutical effect was examined. The obtained results are shown in Table 4. It was suggested that the compound would be effective for remedy of the candidiasis.

TABLE 4

| Amount Administered (mg/kg) | Survival Ratio | Number of Living Cells in Kidney of Survivor Mouse |
|---|---|---|
| control | 0/3 | — |
| 50 | 1/3 | substantially annihilated |
| 100 | 2/3 | " |

EXAMPLE 6

Curative Effect to Trichophytosis

A guinea pig was skin-infected with Trichophyton mentagrophytes, and after two days had passed from the infection, the compound obtained in Example 1 was orally administered in the form of a suspension in gum arabic once a day for 10 days and the pharmaceutical effect was examined. Then, the administraion of the compound was stopped for 3 days and the recovery state was examined. The obtained results are shown in Table 5. It was suggested that the compound would be effective for remedy of the trichophytosis.

TABLE 5

| Amount Administered (mg/kg) | Number of Colonies (cells/ml) in Skin Pieces | |
|---|---|---|
| | after 10 days' administration | after 3 days' stoppage of administration |
| control | $4.1 \times 10^3$ | $3.4 \times 10^3$ |
| 50 | annihilated | annihilated |
| 100 | annihilated | annihilated |

EXAMPLE 7

Toxicity (1) Acute toxicity

The $LD_{50}$ value of the compound obtained in Example 1 at the oral administration is as shown in Table 6. It is seen that the actue toxicity of the compound is very low.

TABLE 6

| Animal | Sex | $LD_{50}$ Value (g/kg) |
|---|---|---|
| mouse | male | 2.95 |
| mouse | female | 3.10 |

(2) Primary irritation to skin

The primary irritation ratio to the skin is as shown in Table 7. It is seen that the compound is a non-irritating substance.

TABLE 7

| Animal | Coating Concentration (%) | Primary Irritation Ratio |
|---|---|---|
| rabbit | 100 | 0.72 |

EXAMPLE 8

Tablet for Oral Administration

A composition comprising 200 mg per tablet of the compound obtained in Example 1 and 800 g per table of a mixture of starch and lactose was prepared and formed into tablets.

EXAMPLE 9

Ointment

A mixture comprising 1% by weight of the compound obtained in Example 1, 25% by weight of liquid paraffin and 74% by weight of white vaseline was kneaded to form an ointment.

EXAMPLE 10

Injection

In 200 ml of physiological saline solution was dissolved 200 mg of the compound obtained in Example 1, and the solution was used as an intravenous drip.

We claim:

1. A chemotherapeutic process for remedying infectious diseases caused by pathogenic true fungi or pathogenic bacteria which comprises administering a composition comprising 1-(4-chlorophenyl)-2-(1H-imidazolyl)-3-(2,4-dichlorophenyl)-2-propen-1-one hydrochloride as the effective ingredient and a pharmaceutical additive to a man or animal infected with a pathogenic true fungus or pathogenic bacterium, the amount administered of the effective ingredient being 1 to 300 mg/kg of the body weight per day.

2. The chemotherapeutic process of claim 1 for remedying infectious diseases caused by pathogenic true fungi.

3. The chemotherapeutic process of claim 2 wherein the pathogenic true fungi is a fungi of the genera Candida, Trichophyton or Microsporum.

4. A chemotherapeutic process of claim 1 for remedying infectious diseases caused by pathogenic bacteria.

5. A chemotherapeutic process according to claim 4 wherein the pathogenic bacteria is a *Staphylococcus, Streptococcus* or *Bacillus subtilis*.

6. A chemotherapeutic process according to claim 1 wherein said composition is administered orally.

7. A chemotherapeutic process according to claim 1 wherein said composition is administered by external application to the infected man or animal.

8. A chemotherapeutic process according to claim 1 wherein the composition is administered to the infected man or animal by injection.

9. A chemotherapeutant composition for remedy of infectious diseases caused by pathogenic true fungi or pathogenic bacteria in men or animals, which comprises a capsule or pill containing a chemotherapeutically effective amount of 1-(4-chlorophenyl)-2-(1H-imidazolyl)-3-(2,4-dichlorophenyl)-2-propen-1-one hydrochloride as the effective ingredient and a pharmaceutical additive wherein the pharmaceutical additive is at least one member selected from the group consisting of excipients, binders, disintegrating agents, lubricants and coating agents.

10. A composition as set forth in claim 9 wherein the concentration of the effective ingredient is from 1 to 80% by weight.

* * * * *